(12) United States Patent
Kim et al.

(10) Patent No.: US 11,248,003 B2
(45) Date of Patent: Feb. 15, 2022

(54) PYRIMIDINE DERIVATIVE HAVING EFFECT OF INHIBITING CANCER CELL GROWTH AND PHARMACEUTICAL COMPOSITION CONTAINING SAME

(71) Applicant: ONCOBIX CO., LTD., Yongin-si (KR)

(72) Inventors: Sung-Eun Kim, Seoul (KR); Sunho Lee, Seoul (KR); Rengasamy Rajesh, Suwon-si (KR); Dae Ho Kang, Goyang-si (KR); Hyung Chui Ryu, Hwaseong-si (KR); Jae-Sun Kim, Suwon-si (KR); Sangryul Lee, Chungju-si (KR); Kyong Cheol Kim, Chungju-si (KR); Jin Kyung Rho, Seoul (KR); Jae Cheol Lee, Seoul (KR)

(73) Assignee: ONCOBIX CO., LTD., Yongin-si (KR)

( * ) Notice: Subject to any disclaimer, the term of this patent is extended or adjusted under 35 U.S.C. 154(b) by 0 days.

(21) Appl. No.: 16/766,350

(22) PCT Filed: Dec. 6, 2018

(86) PCT No.: PCT/KR2018/015437
§ 371 (c)(1),
(2) Date: May 22, 2020

(87) PCT Pub. No.: WO2019/112344
PCT Pub. Date: Jun. 13, 2019

(65) Prior Publication Data
US 2021/0147439 A1    May 20, 2021

(30) Foreign Application Priority Data

Dec. 7, 2017  (KR) .......... 10-2017-0167809
Dec. 5, 2018  (KR) .......... 10-2018-0154838

(51) Int. Cl.
| | |
|---|---|
| C07D 401/14 | (2006.01) |
| C07D 403/14 | (2006.01) |
| A61K 31/506 | (2006.01) |
| A61P 35/00 | (2006.01) |
| C07D 495/04 | (2006.01) |
| C07D 401/12 | (2006.01) |
| C07D 473/16 | (2006.01) |
| C07D 487/04 | (2006.01) |

(52) U.S. Cl.
CPC .......... *C07D 495/04* (2013.01); *A61P 35/00* (2018.01); *C07D 401/12* (2013.01); *C07D 473/16* (2013.01); *C07D 487/04* (2013.01)

(58) Field of Classification Search
CPC .. C07D 401/14; C07D 403/14; A61K 31/506; A61P 35/00
See application file for complete search history.

(56) References Cited

U.S. PATENT DOCUMENTS

| | | |
|---|---|---|
| 8,377,943 B2 | 2/2013 | Sapountzis et al. |
| 2006/0205737 A1 | 9/2006 | Becker et al. |
| 2008/0132504 A1 | 6/2008 | Garcia-Echeverria et al. |
| 2010/0029610 A1 | 2/2010 | Singh et al. |
| 2011/0071158 A1 | 3/2011 | Sapountzis et al. |
| 2011/0098288 A1 | 4/2011 | Major et al. |
| 2012/0202776 A1 | 8/2012 | Wang et al. |
| 2013/0281438 A1 | 10/2013 | Xiao et al. |
| 2017/0012833 A1 | 1/2017 | Kumar et al. |
| 2017/0226065 A1 | 8/2017 | Shonbrunn et al. |
| 2018/0290984 A1 | 10/2018 | Schonbrunn et al. |
| 2018/0312508 A1 | 11/2018 | Deng et al. |

FOREIGN PATENT DOCUMENTS

| | | |
|---|---|---|
| CN | 106188060 A | 12/2016 |
| JP | 2014-501766 A | 1/2014 |
| RU | 2007132161 A | 3/2009 |
| WO | 2005/016894 A1 | 2/2005 |
| WO | 2009/032694 A1 | 3/2009 |
| WO | 2009/032703 A1 | 3/2009 |
| WO | 2009/112490 A1 | 9/2009 |
| WO | 2009/143389 A1 | 11/2009 |
| WO | 2009/158571 A1 | 12/2009 |
| WO | 2010/106097 A1 | 9/2010 |
| WO | 2015/038868 A1 | 3/2015 |
| WO | 2016/022460 A1 | 2/2016 |
| WO | 2017/066428 A1 | 4/2017 |
| WO | 2018/230934 A1 | 12/2018 |

OTHER PUBLICATIONS

H.Choe et al., "Structure—Activity Relationship Study of 2,4-Dianilinopyrimidine Containing Methanesulfonamide (TRE-069) as Potent and Selective Epidermal Growth Factor Receptor T790M/C797S Mutant Inhibitor for Anticancer Treatment", Bulletin of the Korean Chemical Society, Mar. 13, 2017, pp. 1-5 ( 5 pages total).
Henry J. Breslin et al., "Design, Synthesis, and Anaplastic Lymphoma Kinase (ALK) Inhibitory Activity fora Novel Series of 2,4,8,22-Tetraazatetracyclo[14.3.1.1$^{3,7}$.1$^{9,13}$]-docosa-1(20),3(22),4,6,9(21),10,12,16,18-nonaene Macrocycles", Journal of Medicinal Chemistry, vol. 55, 2011, pp. 449-464 (16 pages total).
Gregory R. Ott et al., "Discovery of Clinical Candidate CEP-37440, a Selective Inhibitor of Focal Adhesion Kinase (FAK) and Anaplastic Lymphoma Kinase (ALK)",Journal of Medicinal Chemistry, vol. 59, 2016, pp. 7478-7496 (19 pages total).
J. Guillermo Paez et al., "EGFR Mutations in Lung Cancer: Correlation with Clinical Response to Gefitinib Therapy", SCIENCE, vol. 304. Jun. 4, 2004, pp. 1497-1500 (4 pages total).

(Continued)

*Primary Examiner* — Bruck Kifle
(74) *Attorney, Agent, or Firm* — Sughrue Mion, PLLC

(57) ABSTRACT

A novel pyrimidine derivative compound and a salt thereof are disclosed. The pyrimidine derivative compound effectively inhibits the growth of C797S mutant EGFR-expressed and MET-amplified cancer cells, which are the main resistance mechanisms of third generation EGFR anticancer agents, and thus may be effectively used in the treatment of lung cancer.

15 Claims, 1 Drawing Sheet
Specification includes a Sequence Listing.

(56) References Cited

OTHER PUBLICATIONS

Thomas J. Lynch, M.D., et al., "Activating Mutations in the Epidermal Growth Factor Receptor Underlying Responsiveness of Non-Small-Cell Lung Cancer to Gefitinib", New England Journal of Medicine,, vol. 350, No. 21, May 20, 2004, pp. 2129-2139 (11 pages total).

Helena A. Yu et al., "Analysis of Tumor Specimens at the Time of Acquired Resistance to EGFR-TKI Therapy in 155 Patients with EGFR-Mutant Lung Cancers", Clinical Cancer Research, vol. 19, No. 8, Apr. 15, 2013, pp. 2240-2247 ( 9 pages total).

Wang et al., "EGFR C797S mutation mediates resistance to third-generation inhibitors in T790M-positive non-small cell lung cancer", Journal of Hematology & Oncology, vol. 9, 2016, ( 5 pages total).

Kenneth S Thress et al., "Acquired EGFR C797S mutation mediates resistance to AZD9291 in non-small cell lung cancer harboring EGFR T790M", Nature Medicine, vol. 21, No. 6, 2015, pp. 560-562 ( 5 pages total).

Yubo Wang et al., "Clinical analysis by next-generation sequencing for NSCLC patients with MET amplification resistant to osimertinib", Lung Cancer, vol. 118, 2018, pp. 105-110 (6 p. total).

Carin R. Espenschied et al., "Multigene Panel Testing Provides a New Perspective on Lynch Syndrome", Journal of Clinical Oncology, vol. 35, No. 22, Aug. 1, 2017, (17 pages total).

Zofia Piotrowska et al., "MET amplification (amp) is a major resistance mechanism to osimertinib", Cancer Center, 2017, https://www.chi-med.com/wp-ontent/uploads/2017/06/pre170603-met-amp-resistance.pdf, (1 page total).

Ken Uchibori et al., "Brigatinib combined with anti-EGFR antibody overcomes osimertinib resistance in EGFR-mutated non-small-cell lung cancer", Nature Communications, vol. 8, 2017, pp. 1-16 (16 pages total).

Rohit K Jain et al., "Spotlight on brigatinib and its potential in the treatment of patients with metastatic ALK-positive non-small cell lung cancer who are resistant or intolerant to crizotinib", Lung Cancer: Targets and Therapy, vol. 8, 2017, pp. 169-177 ( 9 pages total).

Yong Jia et al., "Overcoming EGFR(T790M) and EGFR(C797S) resistance with mutant-selective allosteric inhibitors", NATURE, vol. 534, Jun. 2, 2016, pp. 129-132 ( 15 pages total).

International Search Report of PCT/KR2018/015437 dated Mar. 15, 2019 [PCT/ISA/210].

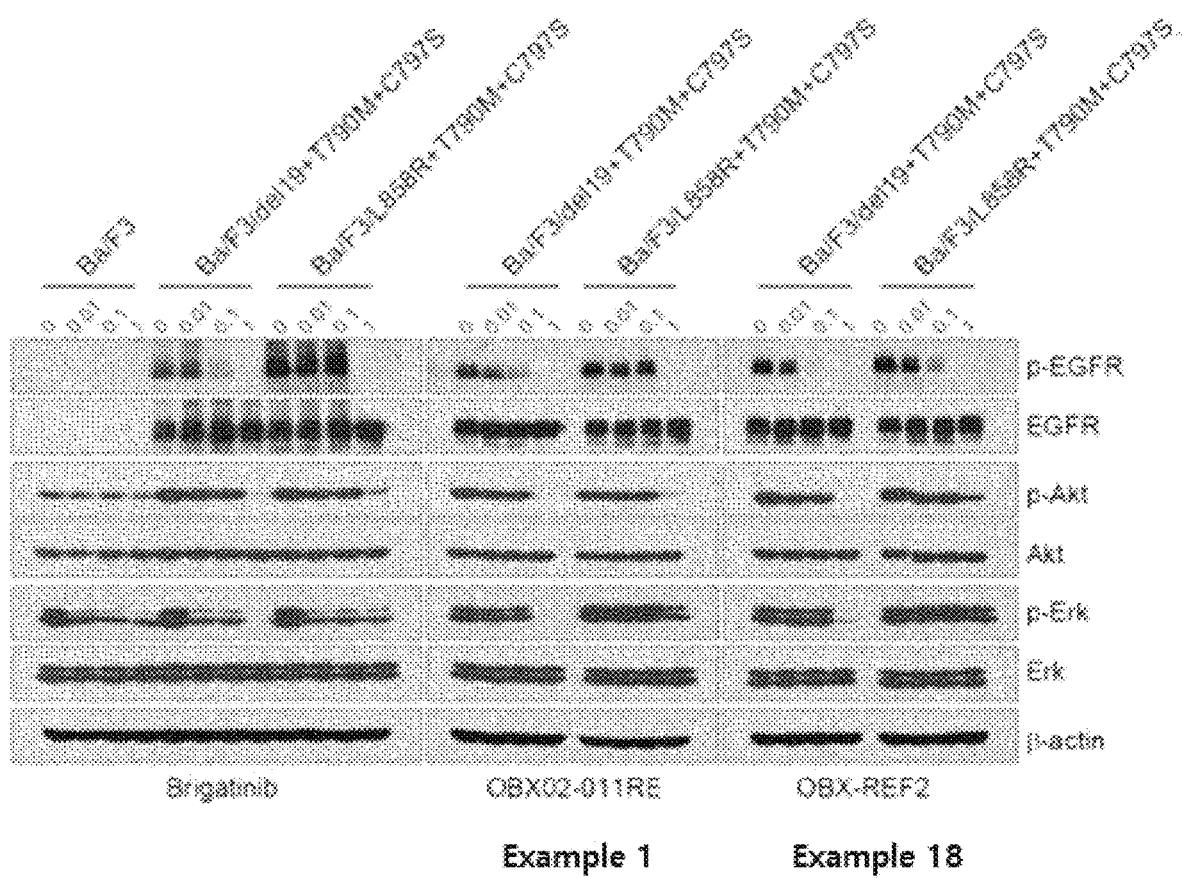

PYRIMIDINE DERIVATIVE HAVING EFFECT OF INHIBITING CANCER CELL GROWTH AND PHARMACEUTICAL COMPOSITION CONTAINING SAME

CROSS REFERENCE TO RELATED APPLICATIONS

This application is a National Stage of International Application No. PCT/KR2018/015437, filed Dec. 6, 2018, claiming priorities to Korean Patent Application No. 10-2017-0167809, filed Dec. 7, 2017 and Korean Patent Application No. 10-2018-0154838, filed Dec. 5, 2018.

TECHNICAL FIELD

The present invention relates to a novel pyrimidine derivative that effectively inhibit cancer cell growth and a pharmaceutical composition comprising the same.

BACKGROUND ART

Activating mutations in the kinase region of an epidermal growth factor receptor (EGFR) have been found to be carcinogenic genes in some non-small cell lung cancer patients, and gefitinib, erlotinib, and the like are used as therapeutic agents, i.e., low molecular weight epidermal growth factor receptor (EGFR) kinase inhibitors for treating them (Science 2004, 304: 1497-500; and New England Journal of Medicine 2004, 350: 2129-39).

The use of gefitinib and erlotinib as therapeutic agents in non-small cell lung cancer patients with identified EGFR activating mutations results in drug resistance in most patients within one year (Clinical Cancer Research 2013, 19: 2240-7). Among these resistance mechanisms, the T790M mutation rate of epidermal growth factor receptor was observed at up to 60%. Therefore, a third generation EGFR inhibitor has been developed that targets the T790M mutant epidermal growth factor receptor (EGFR) in lung cancer.

However, drug resistance of the third generation EGFR inhibitor has been reported, and C797S mutation, MET amplification, and the like have been reported as main resistance mechanisms (J Hematol Oncol. 2016, July 22, 9(1): 59; Nature Medicine 2015, 21: 560-562; Lung Cancer 2018, 118: 105-110; and ASCO 2017, abstract 2572, 9020). C797S mutation and MET amplification have been reported to be found separately but sometimes at the same time (https://www.chi-med.com/wp-content/uploads/2017/06/pre170603-met-amp-resistance.pdf).

The compounds reported in the literature that inhibit C797S are as follows:

Ken Uchibori et al. reported that brigatinib showed activity in C797S mutant cancer (nature communications, 13 Mar. 2017). However, this compound has been reported to have no activity on MET (Lung Cancer: Targets and Therapy 2017, 8: 169-177).

Yong Jia et al. reported an allosteric inhibitor that exhibits activity on an L858R-T790M-C797S-expressed cancer cell line. However, it has not been reported whether this compound is active on a Del19-T790M-C797S-expressed cancer cell line and it has also not been reported whether this compound is active on an MET (Nature 2016 Vol. 534, 129-132).

Kwang-Ho Lee et al. reported TRE-069 showing activity on a T790M/C797S mutant kinase. However, it has not been reported whether this compound effectively inhibits a T790M/C797S mutant cancer cell growth, and it has also not been reported whether this compound is active on MET (Bull. Korean Chem. Soc. 2017, Vol. 38, 1353-1357).

Therefore, there is a need for the development of drugs that effectively inhibit the growth of C797S mutant epidermal growth factor receptor (C797S EGFR) and MET-amplified resistant cancer cells, which are the main resistance mechanisms of the third generation EGFR anticancer agents as described above.

PRIOR ART DOCUMENT

Patent Document

PCT International Publication No. WO2009/143389 A1

DISCLOSURE

Technical Problem

The present inventors sought to develop a novel compound that effectively inhibits C797S mutant EGFR and MET-amplified cancers, which are the main resistance mechanisms of the third generation EGFR anticancer agents. As a result, a novel pyrimidine derivative was found to be effective in treating the cancers. In particular, the novel pyrimidine derivative was found to exhibit excellent effects in the treatment of lung cancer.

Therefore, it is an object of the present invention to provide a novel pyrimidine derivative which is effective in treating cancer.

In addition, it is another object of the present invention to provide a pharmaceutical composition for treating lung cancer, comprising the pyrimidine derivative.

In addition, it is another object of the present invention to provide a pharmaceutical composition for treating C797S mutant EGFR-expressed and MET-amplified lung cancers, which are the main resistance mechanisms of the third generation EGFR anticancer agents, among lung cancers.

Technical Solution

In order to achieve the above objects, the present invention provides a compound represented by following Chemical Formula 1 or a salt thereof:

[Chemical Formula 1]

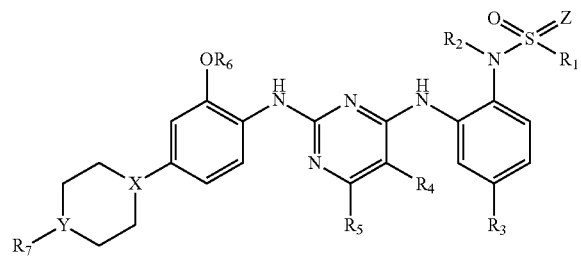

wherein,
X and Y are each independently carbon or nitrogen,
Z is oxygen or a C1 to C4 alkyl group,
$R_1$ is a C1 to C4 alkyl group, a C3 to C6 cycloalkyl group, $CF_3$, or a dimethylamine group,
$R_2$ is a C1 to C4 alkyl group,
$R_3$ is hydrogen or a halogen group, $R_4$ is hydrogen, a halogen group, CN, $CF_3$, a C1 to C4 alkyl group, or an amino carbonyl group, $R_5$ is hydrogen or a C1 to C4 alkyl group, $R_6$ is a C1 to C4 alkyl group, $R_7$ is hydrogen, an amine group substituted with one or more C1 to C4 alkyl groups, or a piperazinyl group unsubstituted or substituted with one or more C1 to C4 alkyl groups, when Z is oxygen, Z forms a double bond with S, which forms a single bond with N, or when Z is a C1 to C4 alkyl group, Z forms a single bond with S, which forms a double bond with N, and $R_4$ and $R_5$ may also be connected to form pyrrole, imidazole, or thiophene.

In addition, the present invention provides the compound represented by Chemical Formula 1 or a salt thereof, which is used for the treatment of lung cancer.

In addition, the present invention provides a pharmaceutical composition for treating lung cancer, comprising the compound represented by Chemical Formula 1 or a pharmaceutically acceptable salt thereof as an active ingredient, and a pharmaceutically acceptable carrier.

In addition, the present invention provides a method of treating an animal suffering from lung cancer, comprising administrating an effective amount of the compound represented by Chemical Formula 1 or a pharmaceutically acceptable salt thereof to the animal.

Advantageous Effects

The novel pyrimidine derivative compound of the present invention provides excellent effects in the treatment of cancer.

In addition, the pharmaceutical composition for treating lung cancer comprising the pyrimidine derivative compound of the present invention provides excellent activities in the treatment of lung cancer, and in particular, effectively inhibits the growth of C797S mutant EGFR and MET-amplified cancer cells caused by the main resistance of the third generation EGFR anticancer agents.

BRIEF DESCRIPTION OF DRAWINGS

FIG. 1 shows the phosphorylation inhibitory effect of compounds of Examples 1 and 18 on a C797S-expressed cancer cell line, which is carried out in Experimental Example 1.

BEST MODE

Hereinafter, the present invention will be described in more detail with reference to embodiments. However, the present invention is not limited by the embodiments that have been represented by way of example, and the present invention is defined only by the scope of the appended claims. In addition, even if the constitution necessary for practicing the present invention, a detailed description of the constitution that may be easily practiced will be omitted.

Unless otherwise stated below, the term "compound of the present invention" or "compound of Chemical Formula 1" is used as a concept including both the compound itself and a salt thereof.

As used herein, the term "alkyl group" refers to a straight and branched hydrocarbon group having the specified number of carbon atoms. The alkyl group may be, for example, methyl, ethyl, n-propyl, i-propyl, n-butyl, s-butyl, i-butyl, t-butyl, and the like.

As used herein, the term "alkylsulfonyl" refers to alkyl-$S(O_2)$—. Wherein, the alkyl is as defined above.

The present invention relates to a compound represented by following Chemical Formula 1 or a salt thereof:

[Chemical Formula 1]

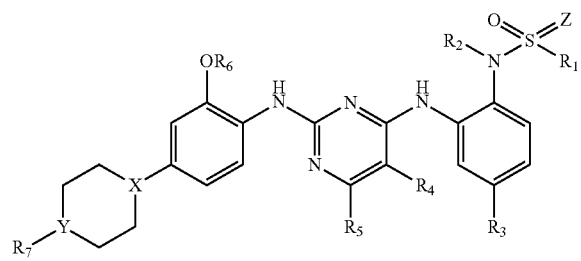

Wherein,

X and Y are each independently carbon or nitrogen,

Z is oxygen or a C1 to C4 alkyl group, $R_1$ is a C1 to C4 alkyl group, a C3 to C6 cycloalkyl group, $CF_3$, or a dimethylamine group, $R_2$ is a C1 to C4 alkyl group, $R_3$ is hydrogen or a halogen group, $R_4$ is hydrogen, a halogen group, CN, $CF_3$, a C1 to C4 alkyl group, or an amino carbonyl group, $R_5$ is hydrogen or a C1 to C4 alkyl group, $R_6$ is a C1 to C4 alkyl group, $R_7$ is hydrogen, an amine group substituted with one or more C1 to C4 alkyl groups, or a piperazinyl group unsubstituted or substituted with one or more C1 to C4 alkyl groups, when Z is oxygen, Z forms a double bond with S, which forms a single bond with N, or when Z is a C1 to C4 alkyl group, Z forms a single bond with S, which forms a double bond with N, and $R_4$ and $R_5$ may also be connected to form pyrrole, imidazole, or thiophene.

The compound represented by Chemical Formula 1 may include the following compounds:

N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide;

N-(2-((5-chloro-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide;

N-(2-((5-chloro-2-((4-(4-(dimethylamino)piperidin-1-yl)-2-methoxyphenyl)amino)pyrimidin-4-yl)amino)phenyl)-N-methylmethanesulfonamide;

N-(2-((5-chloro-2-((2-methoxy-4-(4-(4-methylpiperazin-1-yl)piperidin-1-yl)phenyl)amino)pyrimidin-4-yl)amino)phenyl)-N,P,P-trimethylphosphonic amide;

N-(2-((2-((2-methoxy-4-(4-(4-methylpiperazin-1-yl)piperidin-1-yl)phenyl)amino)-7H-purin-6-yl)amino)phenyl)-N-methylmethanesulfonamide;

N-(2-((2-((2-methoxy-4-(4-(4-methylpiperazin-1-yl)piperidin-1-yl)phenyl)amino)-5-methylpyrimidin-4-yl)amino)phenyl)-N-methylmethanesulfonamide;

N-(2-((5-cyano-2-((2-methoxy-4-(4-(4-methylpiperazin-1-yl)piperidin-1-yl)phenyl)amino)pyrimidin-4-yl)amino)phenyl)-N-methylmethanesulfonamide;

N-(2-((2-((2-methoxy-4-(4-(4-methylpiperazin-1-yl)piperidin-1-yl)phenyl)amino)-5-(trifluoromethyl)pyrimidin-4-yl)amino)phenyl)-N-methylmethanesulfonamide;

2-((2-methoxy-4-(4-(4-methylpiperazin-1-yl)piperidin-1-yl)
phenyl)amino)-4-((2-(N-methylmethylsulfonamido)phe-
nyl)amino)pyrimidin-5-carboxylamide;
N-(2-((5-chloro-2-((2-methoxy-4-(4-(4-methylpiperazin-1-
yl)piperidin-1-yl)phenyl)amino)pyrimidin-4-yl)amino)
phenyl)-N-methylethansulfonamide;
N-(2-((5-chloro-2-((2-methoxy-4-(4-(4-methylpiperazin-1-
yl)piperidin-1-yl)phenyl)amino)pyrimidin-4-yl)amino)
phenyl)-N-methylpropan-2-sulfonamide;
N-(2-((5-chloro-2-((2-methoxy-4-(4-(4-methylpiperazin-1-
yl)piperidin-1-yl)phenyl)amino)pyrimidin-4-yl)amino)
phenyl)-N-methylcyclopropansulfonamide;
N-(2-((5-chloro-2-((2-methoxy-4-(4-(4-methylpiperazin-1-
yl)piperidin-1-yl)phenyl)amino)pyrimidin-4-yl)amino)
phenyl)-1,1,1-trifluoro-N-methylmethanesulfonamide;
N-(2-((5-chloro-2-((2-methoxy-4-(4-(4-methylpiperazin-1-
yl)piperidin-1-yl)phenyl)amino)pyrimidin-4-yl)amino)
phenyl)-N-methyl(-N',N'-dimethyl)sulfonamide;
((2-((5-chloro-2-((2-methoxy-4-(4-(4-methylpiperazin-1-yl)
piperidin-1-yl)phenyl)amino)pyrimidin-4-yl)amino)phe-
nyl)imino)dimethyl-$\lambda^6$-sulfanone;
N-(2-((5-cyano-2-((2-methoxy-4-(4-(4-methylpiperazin-1-
yl)piperidin-1-yl)phenyl)amino)pyrimidin-4-yl)amino)-
4-fluorophenyl)-N-methylmethanesulfonamide;
N-(2-((5-chloro-2-((2-methoxy-4-(piperidin-4-yl)phenyl)
amino)pyrimidin-4-yl)amino)phenyl)-N-methylmethane-
sulfonamide; and
N-(2-((2-((2-methoxy-4-(4-(4-methylpiperazin-1-yl)piperi-
din-1-yl)phenyl)amino)-7H-pyrrolo[2,3-d]pyrimidin-4-
yl)amino)phenyl)-N-methylmethanesulfonamide.

More preferably, the compound represented by Chemical Formula 1 and a salt thereof may be the compound represented by Chemical Formula 1 or a salt thereof, wherein:
X is nitrogen,
Y is carbon
Z is oxygen,
$R_1$ is a C1 to C4 alkyl group,
$R_2$ is a C1 to C4 alkyl group,
$R_3$ is hydrogen or a halogen group,
$R_4$ is a halogen group,
$R_5$ is hydrogen,
$R_6$ is a C1 to C4 alkyl group,
$R_7$ is an amine group substituted with one or more C1 to C4 alkyl groups, or a piperazinyl group unsubstituted or substituted with one or more C1 to C4 alkyl groups.

Still more preferably, the compound represented by Chemical Formula 1 and a salt thereof may be selected from the following compounds:
N-(2-((5-chloro-2-((2-methoxy-4-(4-(4-methylpiperazin-1-
yl)piperidin-1-yl)phenyl)amino)pyrimidin-4-yl)amino)
phenyl)-N-methylmethanesulfonamide;
N-(2-((5-chloro-2-((2-methoxy-4-(4-(4-methylpiperazin-1-
yl)piperidin-1-yl)phenyl)amino)pyrimidin-4-yl)amino)-
4-fluorophenyl)-N-methylmethanesulfonamide; and
N-(2-((5-chloro-2-((4-(4-(dimethylamino)piperidin-1-yl)-2-
methoxyphenyl)amino)pyrimidin-4-yl)amino)phenyl)-N-
methylmethanesulfonamide.

The compound represented by Chemical Formula 1 and a salt thereof according to the present invention may be used to treat cancer. In particular, they may be effectively used in the treatment of lung cancer, and may be effectively used in the treatment of lung cancer having C797S mutant epidermal growth factor receptor (C797S EGFR) and MET-amplified resistant cancer cells, which are the main resistance mechanisms of the third generation EGFR anticancer agents, among lung cancers.

In the present invention, the compound represented by Chemical Formula 1 may be used in the form of a salt derived from an inorganic acid or an organic acid and, for example, may be in the form of a salt derived from one or more acids selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenylacetic acid, cinnamic acid, salicylic acid, methanesulfonic acid, ethanesulfonic acid, benzenesulfonic acid, toluenesulfonic acid, and the like.

In addition, the present invention relates to the compound represented by Chemical Formula 1 or a salt thereof, which is used for the treatment of lung cancer.

In addition, the present invention relates to a pharmaceutical composition for treating lung cancer, comprising the compound represented by Chemical Formula 1 or a pharmaceutically acceptable salt thereof as an active ingredient, and a pharmaceutically acceptable carrier.

In addition, the present invention relates to a method of treating an animal suffering from lung cancer, comprising administrating an effective amount of the compound represented by Chemical Formula 1 or a pharmaceutically acceptable salt thereof to the animal.

The animal may be a human, and the lung cancer may be lung cancer having C797S mutant epidermal growth factor receptor (C797S EGFR) and MET-amplified resistant cancer cells.

The pharmaceutical composition of the present invention may be formulated according to conventional methods, and may be prepared in various oral dosage forms such as tablets, pills, powders, capsules, syrups, emulsions, microemulsions, and the like, or in parenteral dosage forms such as intravenous infusion, subcutaneous infusion, intramuscular infusion, intraperitoneal infusion, transdermal infusion, and direct infusion into tissue.

When the pharmaceutical composition of the present invention is prepared in the form of an oral formulation, ingredients known in the art may be used without limitation as a pharmaceutically acceptable carrier, so long as they do not interfere with the active expression of the active ingredient.

The carrier may include, for example, excipients, diluents, disintegrants, binders, glidants, surfactants, emulsifiers, suspending agents, diluents, and the like, but is not limited thereto.

When the pharmaceutical composition of the present invention is prepared in the form of an injection, ingredients known in the art may be used without limitation as a pharmaceutically acceptable carrier, so long as they do not interfere with the active expression of the active ingredient.

Specifically, the carrier may include, for example, water, saline, aqueous glucose solution, aqueous pseudo-sugar solution, alcohol, glycol, ether (e.g., polyethylene glycol 400), oil, fatty acid, fatty acid ester, glyceride, surfactant, suspending agent, emulsifier, and the like, but is not limited thereto.

The dosage of the pharmaceutical composition of the present invention is preferably determined in consideration of the age, sex, and condition of the patient, the degree of absorption of the active ingredient in the body, the inactivation rate, and the drug to be used in combination, and may be from 0.0001 mg/kg body weight to 100 mg/kg body weight based on the compound of Chemical Formula 1.

MODE FOR CARRYING OUT THE INVENTION

Hereinafter, the present invention will be described in more detail through examples. It will be apparent to those skilled in the art that these examples are only for illustrate the present invention in more detail and the scope of the present invention is not limited to these examples in accordance with the gist of the present invention.

(1) Synthetic Method of Compound Represented by Chemical Formula 1

The compound represented by Chemical Formula 1 according to the present invention may be easily prepared, for example, with reference to the method shown in following Reaction Scheme 1:

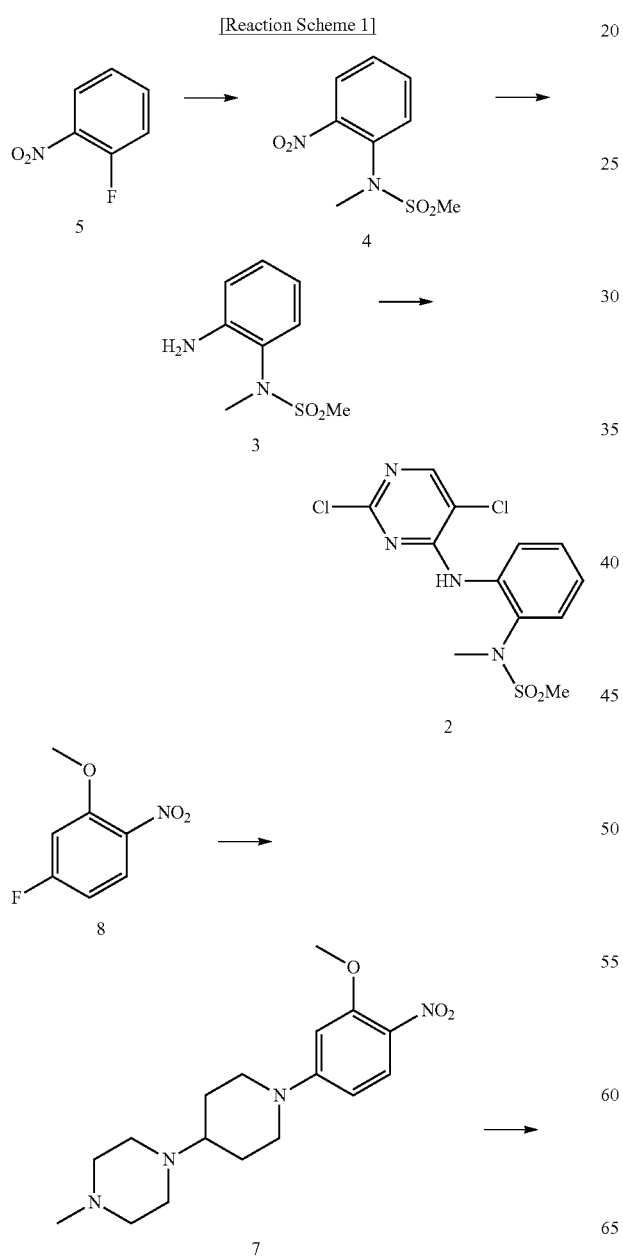

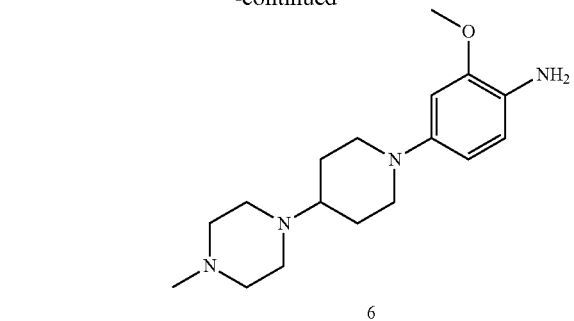

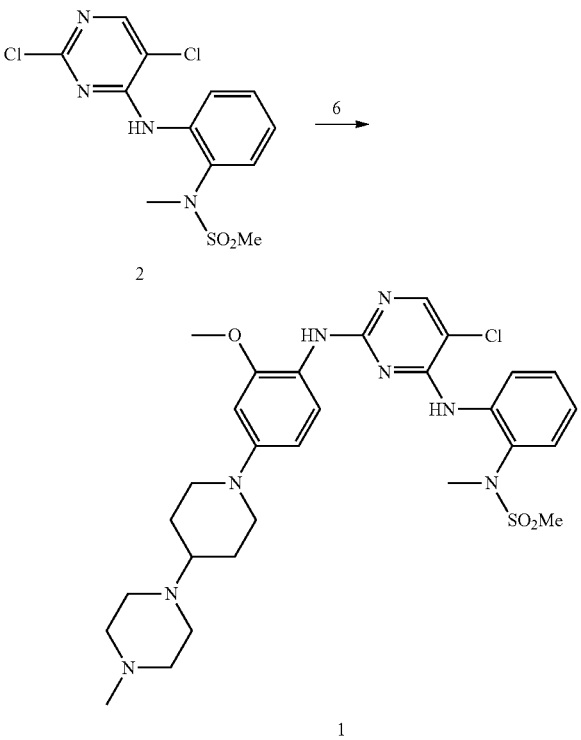

Synthetic Example: Synthesis of N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide 1-1. Preparation of N-methyl-N-(2-nitrophenyl)methanesulfonamide In Reaction Scheme 1 above, 1-fluoro-2-nitrobenzene (3 g, 21.262 mmol) of structure 5 was dissolved in acetonitrile (150 mL), and cesium carbonate (10.4 g, 31.892 mmol) and N-methylmethanesulfonamide were added thereto at room temperature. Then, the mixture was stirred at 80° C. for 12 hours. After stop of the reaction, the reaction solution was cooled to room temperature and filtered, and then the filtrate was evaporated under reduced pressure to give N-methyl-N-(2-nitrophenyl)methanesulfonamide (compound 4). The obtained compound was used in the next reaction without separate separation process.

1-2. Preparation of N-(2-aminophenyl)-N-methylmethanesulfonamide

The N-methyl-N-(2-nitrophenyl)methanesulfonamide (4.5 g, 19.545 mmol) was dissolved in methanol (100 mL)

and dichloromethane (50 mL), and 10% palladium/charcoal (0.416 g, 3.909 mmol) was added thereto. The mixture was stirred for 2 hours under hydrogen atmosphere. After stop of the reaction, the reaction solution was filtered through celite. The filtrate was evaporated under reduced pressure, and then solidified with ethylether and n-pentane, which filtered to give N-(2-aminophenyl)-N-methylmethanesulfonamide (compound 3). The obtained compound was used in the next reaction without separate separation process.

1-3. Preparation of N-(2-((2,5-dichloropyrimidin-4-yl)amino)phenyl)-N-methylmethanesulfonamide N-(2-aminophenyl)-N-methylmethanesulfonamide (8.3 g, 41.446 mmol) prepared above was dissolved in isopropyl alcohol (200 mL), and 2,4,5-trichloropyrimidine (12.163 g, 66.314 mmol) and N,N-diisopropylethylamine (21.428 g, 166 mmol) were added thereto at room temperature. After the reaction was stopped by stirring at 90° C. for 12 hours, the reaction solution was evaporated under reduced pressure and extracted with water and dichloromethane. The organic layer was washed with 2N hydrochloric acid and evaporated under reduced pressure to give N-(2-((2,5-dichloropyrimidin-4-yl)amino)phenyl)-N-methylmethanesulfonamide (compound 2). The obtained compound was used in the next reaction without separate separation process.

1-4. Preparation of 1-(1-(3-methoxy-4-nitrophenyl)piperidin-4-yl)-4-methylpiperazine 4-fluoro-2-methoxy-1-nitrobenzene (5 g, 29.218 mmol) of structure 8 in Reaction Scheme 1 above was dissolved in acetonitrile (100 mL), and potassium carbonate (8.076 g, 58.435 mmol) and piperazine intermediate (5.4 g, 29.218 mmol) were added thereto at room temperature. After the reaction was stopped by stirring at 90° C. for 12 hours, the temperature was lowered to room temperature and the reaction solution was filtered. The filtrate was evaporated under reduced pressure to give 1-(1-(3-methoxy-4-nitrophenyl)piperidin-4-yl)-4-methylpiperazine (compound 7). The obtained compound was used in the next reaction without separate separation process.

1-5. Preparation of 2-methoxy-4-(4-(4-methylpiperazin-1-yl)piperidin-1-yl)aniline 1-(1-(3-methoxy-4-nitrophenyl)piperidin-4-yl)-4-methylpiperazine (8.4 g, 25.118 mmol) prepared above was dissolved in a mixed solvent of methanol (250 mL) and dichloromethane (50 mL), and 10% palladium/charcoal (0.802 g, 7.353 mmol) was added thereto. After the reaction was stopped by stirring for 2 hours under hydrogen atmosphere, the reaction solution was filtered through celite. The filtrate was evaporated under reduced pressure, and then solidified with n-hexane to give 2-methoxy-4-(4-(4-methylpiperazin-1-yl)piperidin-1-yl)aniline (compound 6). The obtained compound was used in the next reaction without separate separation process.

1-6. Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide N-(2-((2,5-dichloropyrimidin-4-yl)amino)phenyl)-N-methylmethanesulfonamide (11 g, 31.681 mmol) prepared above was dissolved in isopropyl alcohol (150 mL), and 2-methoxy-4-(4-(4-methylpiperazin-1-yl)piperidin-1-yl)aniline (7.0 g, 23.127 mmol) and p-toluenesulfonyl acid (6.0 g, 31.681 mmol) were added thereto at room temperature. After the reaction was stopped by stirring at 90° C. for 12 hours, the reaction solution was evaporated under reduced pressure to remove the solvent, and extracted with water and a 10% mixed solution of methanol/dichloromethane. The separated organic layer was evaporated under reduced pressure and subjected to column chromatography to give N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide (compound 1). (5-10% ammonia/methyl alcohol/dichloromethane)

(2) Synthetic Method of N-methylalkylsulfonamide

To 2M methylamine (2.6 eq) dissolved in tetrahydrofuran is slowly added sulfonyl chloride (1.0 eq) at 0° C. The temperature is warmed to room temperature and stirred for 4 hours at the same temperature. After stop of the reaction, the reaction solution was evaporated under reduced pressure and extracted with 2N hydrochloric acid and MC. The separated organic layer was evaporated under reduced pressure to give the title compound.

(3) Preparative Method of Final Compounds

<Method 1>

Pyrimidine derivative (1.37 eq) is dissolved in isopropyl alcohol, and aniline derivative (1.0 eq) and para-toluenesulfonyl acid (1.37 eq) are added thereto at room temperature. The mixture was stirred at 90° C. for 12 hours. After stop of the reaction, the reaction solution is evaporated under reduced pressure to remove the solvent, and extracted with water and a mixed solution of 10% methanol/dichloromethane. The separated organic layer was evaporated under reduced pressure and subjected to column chromatography to give the title compound (5-10% ammonia/methyl alcohol/dichloromethane).

<Method 2>

Pyrimidine derivative (1.0 eq) is dissolved in 1,4-dioxane, and aniline derivative (1.0 eq), palladium acetate (0.14 eq), 2,2'-bis(diphenylphosphino)-1,1'-binaphthyl (BINAP, 0.28 eq), and potassium carbonate (2.3 eq) are added thereto at room temperature. After the reaction was stopped by stirring under reflux for 12 hours, the temperature is lowered to room temperature. The reaction solution was filtered through celite, and then extracted with water and ethyl acetate, and the separated organic layer was evaporated under reduced pressure and subjected to column chromatography to give the title compound (5-10% methyl alcohol/dichloromethane).

(4) Deprotective Method of Compound Having Protecting Group

<Method 1>

The compound having a protecting group was dissolved in 4M hydrochloric acid (1,4-dioxane). After the reaction was stopped by stirring for 3 hours at room temperature, the reaction solution was neutralized with 1N sodium hydroxide solution and extracted with ethyl acetate. The separated organic layer was evaporated under reduced pressure and subjected to column chromatography to give the title compound.

<Method 2> The compound having a protecting group was dissolved in a mixed solvent of methanol, 1,4-dioxane, and water (3:3:1). Cesium carbonate (10.0 eq) was added thereto at room temperature and the mixture was stirred at 80° C. for 3 hours. After stop of the reaction, the temperature was lowered to room temperature, and then water was added thereto. The resulting solid was filtered and dried. The solid was separated by column chromatography to give the title compound.

Example 1: Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide

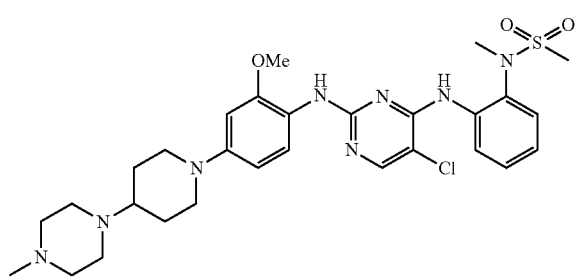

The final compound was prepared by Method 1.

Yield: 48.2%; white solid; $^1$H NMR (400 MHz, Chloroform-d) δ 8.41 (dd, J=8.3, 1.5 Hz, 1H), 8.28 (s, 1H), 8.05 (s, 1H), 8.00 (d, J=8.8 Hz, 1H), 7.37 (ddd, J=8.5, 7.3, 1.5 Hz, 1H), 7.31 (dd, J=8.0, 1.5 Hz, 1H), 7.23 (s, 1H), 7.16 (td, J=7.6, 1.5 Hz, 1H), 6.53 (d, J=2.5 Hz, 1H), 6.44 (dd, J=8.8, 2.5 Hz, 1H), 3.84 (s, 3H), 3.63 (d, J=12.0 Hz, 2H), 3.27 (s, 3H), 2.98 (s, 3H), 2.73-2.63 (m, 2H), 2.64 (s, 4H), 2.37 (tt, J=11.9, 3.8 Hz, 1H), 2.29 (s, 3H), 1.94 (d, J=12.4 Hz, 2H), 1.70 (qd, J=12.0, 3.8 Hz, 4H).

Example 2: Preparation of N-(2-((5-chloro-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide

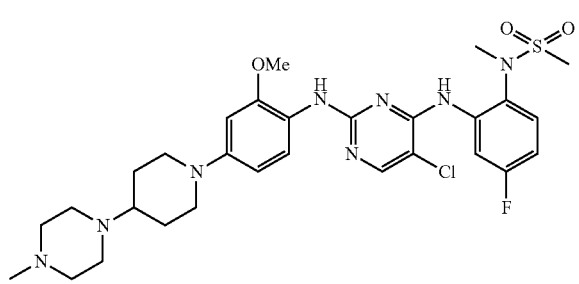 [SMILES: COc1cc(N2CCC(N3CCN(C)CC3)CC2)ccc1Nc1ncc(Cl)c(Nc2cc(F)ccc2N(C)S(C)(=O)=O)n1]

The final compound was prepared by Method 2.

Yield: 15.9%; white solid; $^1$H NMR (400 MHz, DMSO-d6): δ 8.34 (s, 1H), 8.26 (s, 1H), 8.16 (bs, 1H), 8.09 (s, 1H), 7.59 (dd, J=8.9, 5.9 Hz, 1H), 7.23 (d, J=8.6 Hz, 1H), 6.90 (td, J=8.3, 3.1 Hz, 1H), 6.58 (d, J=2.5 Hz, 1H), 6.42 (dd, J=8.7, 2.5 Hz, 1H), 3.71-3.65 (m, 5H), 3.14 (s, 3H), 3.08 (s, 3H), 2.68-2.56 (m, 2H), 2.51-2.42 (m, 4H), 2.36-2.18 (m, 5H), 2.11 (s, 3H), 1.81 (d, J=12.2 Hz, 2H), 1.47 (m, 2H). MS: ESI m/z 633.2 [M+H]+.

Example 3: Preparation of N-(2-((5-chloro-2-((4-(4-(dimethylamino)piperidin-1-yl)-2-methoxyphenyl)amino)pyrimidin-4-yl)amino)phenyl)-N-methylmethanesulfonamide

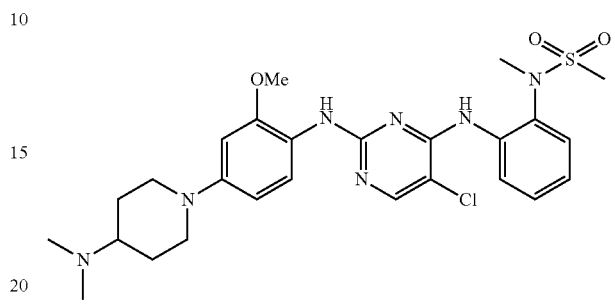

The final compound was prepared by Method 2.

Yield: 17.7%; off-white solid; $^1$H NMR (400 MHz, DMSO-d6): δ 8.24 (s, 2H), 8.06 (d, J=1.9 Hz, 2H), 7.54 (dd, J=7.9, 1.6 Hz, 1H), 7.33 (d, J=8.7 Hz, 1H), 7.21 (t, J=7.9 Hz, 1H), 7.12 (td, J=7.6, 1.5 Hz, 1H), 6.58 (d, J=2.5 Hz, 1H), 6.42 (dd, J=8.8, 2.5 Hz, 1H), 3.71 (s, 3H), 3.66 (d, J=12.3 Hz, 2H), 3.14 (s, 3H), 3.06 (s, 3H), 2.69-2.57 (m, 2H), 2.17 (m, 7H), 1.81 (d, J=12.3 Hz, 2H), 1.46 (qd, J=11.9, 3.8 Hz, 2H).

Example 4: Preparation of N-(2-((5-chloro-2-((2-methoxy-4-(4-(4-methylpiperazin-1-yl)piperidin-1-yl)phenyl)amino)pyrimidin-4-yl)amino)phenyl)-N,P,P-trimethylphosphonic amide

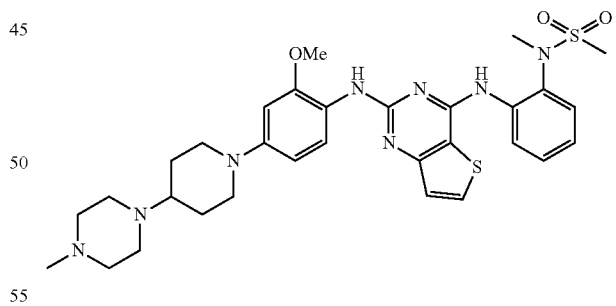

The final compound was prepared by Method 2.

Yield: 18.5%; yellow solid; $^1$H NMR (400 MHz, DMSO-d6) δ 8.41 (s, 1H), 8.03-7.96 (m, 2H), 7.74 (d, J=8.7 Hz, 1H), 7.56 (dd, J=7.9, 1.6 Hz, 1H), 7.48 (s, 1H), 7.33 (ddd, J=8.2, 7.3, 1.6 Hz, 1H), 7.24 (td, J=7.7, 1.6 Hz, 1H), 7.14 (d, J=5.4 Hz, 1H), 6.57 (d, J=2.5 Hz, 1H), 6.38 (dd, J=8.9, 2.5 Hz, 1H), 3.75 (s, 3H), 3.62 (d, J=12.1 Hz, 2H), 3.12 (s, 3H), 3.01 (s, 3H), 2.59 (t, J=11.9 Hz, 2H), 2.51-2.42 (m, 4H), 2.29 (s, 5H), 2.12 (s, 3H), 1.81 (d, J=12.6 Hz, 2H), 1.48 (q, J=13.0, 11.8 Hz, 2H). MS: ESI m/z 637.2 [M+H]+.

Example 5: Preparation of N-(2-((2-((2-methoxy-4-(4-(4-methylpiperazin-1-yl)piperidin-1-yl)phenyl)amino)-7H-purin-6-yl)amino)phenyl)-N-methyl-methanesulfonamide The final compound was prepared by Method 1.

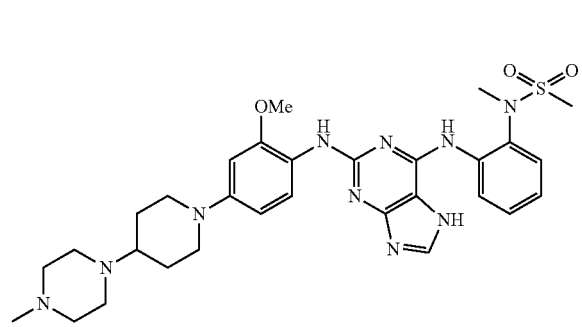 [SMILES: COc1cc(N2CCC(N3CCN(C)CC3)CC2)ccc1Nc1nc(Nc2ccccc2N(C)S(C)(=O)=O)c2sccc2n1]

Yield: 51.3%; pale yellow solid; ¹H NMR (400 MHz, Chloroform-d) δ 8.66 (dd, J=8.4, 1.5 Hz, 1H), 8.44 (s, 1H), 7.99 (d, J=8.7 Hz, 1H), 7.44-7.29 (m, 2H), 7.10 (ddd, J=8.0, 7.3, 1.5 Hz, 1H), 7.04 (s, 1H), 6.56 (d, J=2.5 Hz, 1H), 6.48 (dd, J=8.8, 2.5 Hz, 1H), 3.86 (s, 3H), 3.63 (d, J=12.0 Hz, 2H), 3.28 (s, 3H), 3.01 (s, 3H), 2.73-2.57 (m, 6H), 2.55-2.27 (m, 2H), 2.15 (s, 3H), 2.11-1.89 (m, 6H), 1.69 (qd, J=12.2, 3.9 Hz, 2H).

Example 6: Preparation of N-(2-((2-((2-methoxy-4-(4-(4-methylpiperazin-1-yl)piperidin-1-yl)phenyl)amino)-5-methylpyrimidin-4-yl)amino)phenyl)-N-methylmethanesulfonamide

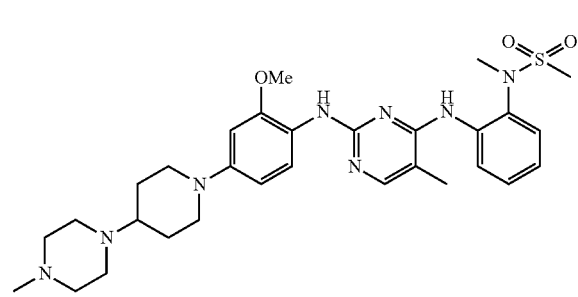

The final compound was prepare by Method 2.

Yield: 29.3%; beige color solid; ¹H NMR (400 MHz, DMSO-d6): δ 8.98 (bs, 1H), 8.36 (s, 1H), 7.91 (bs, 1H), 7.78 (s, 1H), 7.51-7.42 (m, 1H), 7.16-7.00 (m, 3H), 6.61 (d, J=2.5 Hz, 1H), 6.44 (dd, J=8.7, 2.5 Hz, 1H), 3.75-3.70 (m, 5H), 3.15 (s, 3H), 3.01 (s, 3H), 2.68 (t, J=11.9 Hz, 3H), 2.51-2.42 (m, 4H), 2.41 (s, 3H), 2.38-2.20 (m, 5H), 2.13 (s, 3H), 1.81 (d, J=12.5 Hz, 2H), 1.48 (m, 2H). MS: ESI m/z 595.1 [M+H]+.

Example 7: Preparation of N-(2-((5-cyano-2-((2-methoxy-4-(4-(4-methylpiperazin-1-yl)piperidin-1-yl)phenyl)amino)pyrimidin-4-yl)amino)phenyl)-N-methylmethanesulfonamide The final compound was prepared by Method 2.

Yield: 33.3%; beige color solid; ¹H NMR (400 MHz, DMSO-d6): δ 8.96 (bs, 1H), 8.37 (s, 1H), 8.26 (s, 1H), 7.91 (bs, 1H), 7.51-7.42 (m, 1H), 7.16-7.00 (m, 3H), 6.61 (d, J=2.5 Hz, 1H), 6.44 (dd, J=8.7, 2.5 Hz, 1H), 3.75 (d, J=12.2 Hz, 2H), 3.70 (s, 3H), 3.10 (s, 3H), 3.02 (s, 3H), 2.68 (t, J=11.9 Hz, 3H), 2.51-2.42 (m, 4H), 2.38-2.20 (m, 5H), 2.11 (s, 3H), 1.82 (d, J=12.5 Hz, 2H), 1.48 (m, 2H). MS: ESI m/z 606.2 [M+H]+.

Example 8: Preparation of N-(2-((2-((2-methoxy-4-(4-(4-methylpiperazin-1-yl)piperidin-1-yl)phenyl)amino)-5-(trifluoromethyl)pyrimidin-4-yl)amino)phenyl)-N-methylmethanesulfonamide Yield: 20.6%; beige color solid; ¹H NMR (400 MHz, DMSO-d6): δ 9.02 (bs, 1H), 8.37 (s, 1H), 8.26 (bs, 1H), 7.90 (s, 1H), 7.51-7.42 (m, 1H), 7.16-7.00 (m, 3H), 6.60 (d, J=2.5 Hz, 1H), 6.47 (dd, J=8.7, 2.5 Hz, 1H), 3.77-3.70 (m, 5H), 3.10 (s, 3H), 3.02 (s, 3H), 2.68 (t, J=11.9 Hz, 3H), 2.51-2.42 (m, 4H), 2.39-2.21 (m, 5H), 2.14 (s, 3H), 1.81 (d, J=12.5 Hz, 2H), 1.49 (m, 2H). MS: ESI m/z 649.2 [M+H]+.

Example 9: Preparation of 2-((2-methoxy-4-(4-(4-methylpiperazin-1-yl)piperidin-1-yl)phenyl)amino)-4-((2-(N-methylmethylsulfonamido)phenyl)amino)pyrimidin-5-carboxylamide

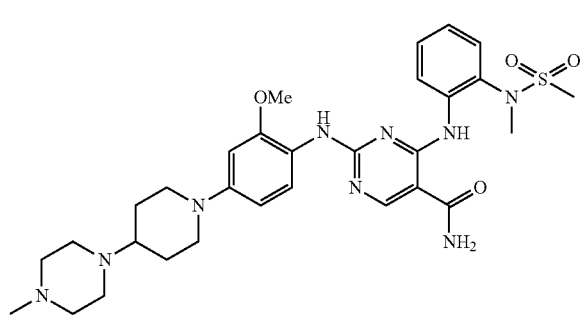 [SMILES: COc1cc(N2CCC(N3CCN(C)CC3)CC2)ccc1Nc1ncc(C(N)=O)c(Nc2ccccc2N(C)S(C)(=O)=O)n1]

Yield: 17.5%; beige color solid; ¹H NMR (400 MHz, DMSO-d6): δ 8.94 (bs, 1H), 8.32 (s, 1H), 8.28 (s, 1H), 7.96 (s, 2H), 7.87 (bs, 1H), 7.51-7.42 (m, 1H), 7.16-7.00 (m, 3H), 6.61 (d, J=2.5 Hz, 1H), 6.44 (dd, J=8.7, 2.5 Hz, 1H), 3.75 (d, J=12.2 Hz, 2H), 3.68 (s, 3H), 3.07 (s, 3H), 3.00 (s, 3H), 2.68 (t, J=11.9 Hz, 3H), 2.51-2.42 (m, 4H), 2.42-2.22 (m, 5H), 2.07 (s, 3H), 1.81 (m, 2H), 1.48 (m, 2H). MS: ESI m/z 624.1 [M+H]+.

Example 10: Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methylethanesulfonamide

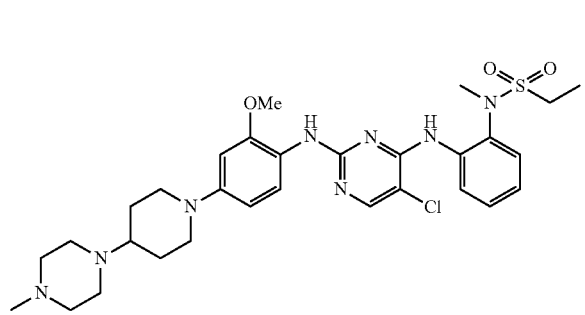 [SMILES: CCS(=O)(=O)N(C)c1ccccc1Nc1nc(Nc2ccc(N3CCC(N4CCN(C)CC4)CC3)cc2OC)ncc1Cl]

The final compound was prepared by Method 1.

Yield: 55.6%; pale yellow solid; ¹H NMR (400 MHz, Chloroform-d) δ 8.42-8.29 (m, 2H), 8.10-7.98 (m, 2H), 7.42-7.30 (m, 2H), 7.23-7.13 (m, 1H), 6.51 (t, J=3.0 Hz, 1H), 6.43 (dd, J=8.8, 2.5 Hz, 1H), 3.84 (s, 3H), 3.63 (d, J=12.1 Hz, 2H), 3.28 (s, 3H), 3.15 (q, J=7.4 Hz, 2H), 2.77 (s, 3H), 2.74-2.63 (m, 5H), 2.45 (d, J=12.4 Hz, 1H), 2.40 (s, 3H), 1.99 (dd, J=19.2, 10.0 Hz, 4H), 1.74 (td, J=12.0, 3.8 Hz, 3H), 1.45 (t, J=7.4 Hz, 3H).

Example 11: Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methylpropan-2-sulfonamide The final compound was prepared by Method 1.

Yield: 54.4%; off-white solid; ¹H NMR (400 MHz, Chloroform-d) δ 8.34 (s, 1H), 8.32-8.19 (m, 1H), 8.10-7.99 (m, 2H), 7.43-7.32 (m, 2H), 7.28 (d, J=7.8 Hz, 7H), 7.24-7.03 (m, 2H), 6.54-6.48 (m, 1H), 6.41 (dd, J=8.8, 2.5 Hz, 1H), 3.84 (s, 3H), 3.78 (s, 1H), 3.64 (s, 1H), 3.42 (p, J=6.8 Hz, 2H), 3.29 (s, 3H), 2.88 (s, 3H), 2.86-2.76 (m, 4H), 2.68 (t, J=11.8 Hz, 3H), 2.49 (s, 3H), 1.74 (d, J=11.6 Hz, 3H), 1.70 (bs, 2H), 1.46 (d, J=6.8 Hz, 6H).

Example 12: Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methylcyclopropansulfonamide

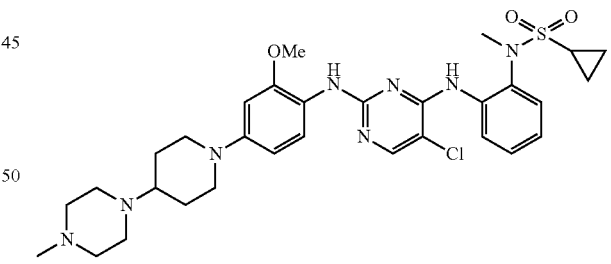

The final compound was prepare by Method 1.

Yield: 50.7%; pale yellow solid; ¹H NMR (400 MHz, Chloroform-d) δ 8.40 (dd, J=8.3, 1.5 Hz, 1H), 8.32 (s, 1H), 8.12-8.00 (m, 2H), 7.51-7.36 (m, 2H), 7.34 (d, J=1.6 Hz, 1H), 7.22-7.04 (m, 2H), 6.55-6.41 (m, 2H), 3.85 (s, 3H), 3.79 (s, 1H), 3.64 (d, J=12.1 Hz, 2H), 3.28 (s, 3H), 3.26 (d, J=6.3 Hz, 1H), 2.81 (d, J=25.8 Hz, 4H), 2.69 (t, J=11.9 Hz, 2H), 2.50 (td, J=8.0, 3.9 Hz, 2H), 2.46 (s, 3H), 1.99 (dd, J=11.3, 4.7 Hz, 2H), 1.75 (t, J=12.1 Hz, 2H), 1.26-1.15 (m, 2H), 1.01 (s, 2H).

Example 13: Preparation of N-(2-((5-chloro-2-((2-methoxy-4-(4-(4-methylpiperazin-1-yl)piperidin-1-yl)phenyl)amino)pyrimidin-4-yl)amino)phenyl)-1,1,1-trifluoro-N-methylmethanesulfonamide

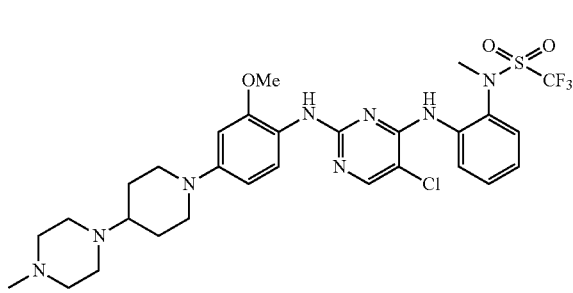 [SMILES: COc1cc(N2CCC(N3CCN(C)CC3)CC2)ccc1Nc1ncc(Cl)c(Nc2ccccc2N(C)S(=O)(=O)C(F)(F)F)n1]

Yield: 21.3%; light yellow solid; ¹H NMR (400 MHz, Chloroform-d) δ 8.41 (dd, J=8.3, 1.5 Hz, 1H), 8.28 (s, 1H), 8.05 (s, 1H), 8.00 (d, J=8.8 Hz, 1H), 7.37 (ddd, J=8.5, 7.3, 1.5 Hz, 1H), 7.31 (dd, J=8.0, 1.5 Hz, 1H), 7.23 (s, 1H), 7.16 (td, J=7.6, 1.5 Hz, 1H), 6.53 (d, J=2.5 Hz, 1H), 6.44 (dd, J=8.8, 2.5 Hz, 1H), 3.84 (s, 3H), 3.63 (d, J=12.0 Hz, 2H), 3.51 (s, 3H), 2.73-2.63 (m, 2H), 2.64 (s, 4H), 2.37 (tt, J=11.9, 3.8 Hz, 1H), 2.24 (s, 3H), 1.94 (d, J=12.4 Hz, 2H), 1.70 (qd, J=12.0, 3.8 Hz, 4H).

Example 14: Preparation of N-(2-((5-chloro-2-((2-methoxy-4-(4-(4-methylpiperazin-1-yl)piperidin-1-yl)phenyl)amino)pyrimidin-4-yl)amino)phenyl)-N-methyl(-N',N'-dimethyl)sulfonamide

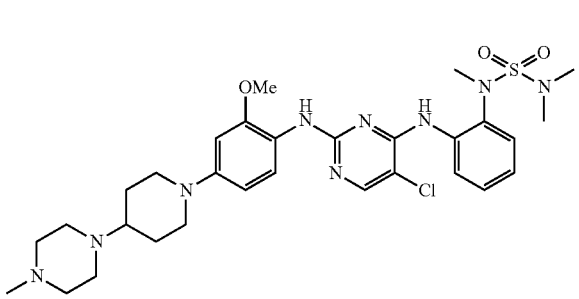

Yield: 17.4%; beige color solid; ¹H NMR (400 MHz, Chloroform-d) δ 8.42 (dd, J=8.3, 1.5 Hz, 1H), 8.27 (s, 1H), 8.01 (s, 1H), 7.96 (d, J=8.8 Hz, 1H), 7.35 (ddd, J=8.5, 7.3, 1.5 Hz, 1H), 7.30 (dd, J=8.0, 1.5 Hz, 1H), 7.23 (s, 1H), 7.16 (td, J=7.6, 1.5 Hz, 1H), 6.53 (d, J=2.5 Hz, 1H), 6.44 (dd, J=8.8, 2.5 Hz, 1H), 3.84 (s, 3H), 3.63 (d, J=12.0 Hz, 2H), 2.97 (s, 3H), 2.74 (s, 6H), 2.73-2.63 (m, 2H), 2.64 (s, 4H), 2.37 (tt, J=11.9, 3.8 Hz, 1H), 2.29 (s, 3H), 1.94 (d, J=12.4 Hz, 2H), 1.70 (qd, J=12.0, 3.8 Hz, 4H).

Example 15: Preparation of ((2-((5-chloro-2-((2-methoxy-4-(4-(4-methylpiperazin-1-yl)piperidin-1-yl)phenyl)amino)pyrimidin-4-yl)amino)phenyl)imino)dimethyl-$\lambda^6$-sulfanone Yield: 12.9%; beige color solid; ¹H NMR (400 MHz, Chloroform-d) δ 8.46 (dd, J=8.3, 1.5 Hz, 1H), 8.30 (s, 1H), 8.02 (s, 1H), 8.00 (d, J=8.8 Hz, 1H), 7.37 (m, 1H), 7.31 (dd, J=8.0, 1.5 Hz, 1H), 7.23 (s, 1H), 7.16 (td, J=7.6, 1.5 Hz, 1H), 6.53 (d, J=2.5 Hz, 1H), 6.48 (dd, J=8.8, 2.5 Hz, 1H), 3.85 (s, 3H), 3.63 (d, J=12.0 Hz, 2H), 3.29 (s, 6H), 2.73-2.63 (m, 2H), 2.64 (s, 4H), 2.37 (tt, J=11.9, 3.8 Hz, 1H), 2.12 (s, 3H), 1.94 (d, J=12.4 Hz, 2H), 1.70 (m, 4H).

Example 16: Preparation of N-(2-((5-cyano-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide The final compound was prepared by Method 2.

Yield: 23.1%; off-white solid; ¹H NMR (400 MHz, DMSO-d6): δ 9.14 (bs, 1H), 8.41 (s, 1H), 8.24 (d, J=1.3 Hz, 1H), 7.83 (bs, 1H), 7.52 (dd, J=8.8, 5.9 Hz, 1H), 7.07 (d, J=8.6 Hz, 1H), 6.83 (td, J=8.3, 3.0 Hz, 1H), 6.59 (d, J=2.5 Hz, 1H), 6.45 (dd, J=8.7, 2.5 Hz, 1H), 3.74-3.70 (m, 5H), 3.10 (s, 3H), 3.03 (s, 3H), 2.65 (t, J=11.5 Hz, 2H), 2.51-2.42 (m, 4H), 2.27 (m, 5H), 2.11 (s, 3H), 1.81 (d, J=12.4 Hz, 2H), 1.55-1.40 (m, 2H).

Example 17: Preparation of N-(2-((5-chloro-2-((2-methoxy-4-(piperidin-4-yl)phenyl)amino)pyrimidin-4-yl)amino)phenyl)-N-methylmethanesulfonamide

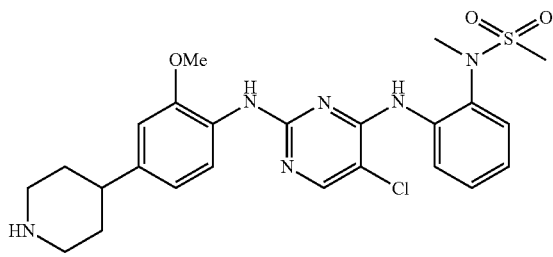 [SMILES: COc1cc(C2CCNCC2)ccc1Nc1ncc(Cl)c(Nc2ccccc2N(C)S(C)(=O)=O)n1]

The final compound proceeded to Preparative Method 2 and was deprotected by Deprotective Method 2.

Yield: 60.8%; tan color solid; $^1$H NMR (400 MHz, Methanol-d4) δ 8.15 (dt, J=8.6, 2.2 Hz, 1H), 8.02 (d, J=0.5 Hz, 1H), 7.82 (d, J=8.3 Hz, 1H), 7.55 (dd, J=8.0, 1.5 Hz, 1H), 7.37 (ddd, J=9.5, 6.2, 1.6 Hz, 1H), 7.26 (td, J=7.7, 1.6 Hz, 1H), 6.84 (d, J=1.9 Hz, 1H), 6.66 (dd, J=8.3, 1.9 Hz, 1H), 3.85 (s, 3H), 3.22 (s, 3H), 3.10 (d, J=12.3 Hz, 2H), 3.01 (s, 3H), 2.69 (td, J=12.4, 2.6 Hz, 2H), 2.60 (tt, J=12.0, 3.6 Hz, 1H), 1.78 (d, J=12.8 Hz, 2H), 1.63 (qd, J=12.5, 4.1 Hz, 2H). MS: ESI m/z 517.1 [M+H]+.

Example 18: Preparation of N-(2-((2-((2-methoxy-4-(4-(4-methylpiperazin-1-yl)piperidin-1-yl)phenyl)amino)-7H-pyrrolo[2,3-d]pyrimidin-4-yl)amino)phenyl)-N-methylmethanesulfonamide

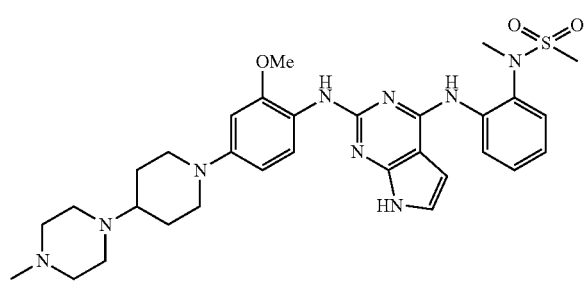 [SMILES: COc1cc(N2CCC(N3CCN(C)CC3)CC2)ccc1Nc1nc(Nc2ccccc2N(C)S(C)(=O)=O)c2cc[nH]c2n1]

The final compound proceeded to Preparative Method 2 and was deprotected by Deprotective Method 2.

Yield: 47.1%; tan color solid; $^1$H NMR (400 MHz, DMSO-d6) δ 11.22 (s, 1H), 8.21 (dd, J=8.2, 1.5 Hz, 1H), 8.17 (s, 1H), 7.90 (d, J=8.7 Hz, 1H), 7.53 (dd, J=7.9, 1.6 Hz, 1H), 7.36-7.28 (m, 1H), 7.19 (s, 1H), 7.14 (td, J=7.6, 1.5 Hz, 1H), 6.87 (dd, J=3.5, 2.2 Hz, 1H), 6.57 (d, J=2.6 Hz, 1H), 6.40 (dd, J=8.8, 2.5 Hz, 1H), 6.17 (dd, J=3.5, 1.9 Hz, 1H), 3.77 (s, 3H), 3.61 (d, J=12.1 Hz, 2H), 3.15 (s, 3H), 3.05 (s, 3H), 2.63-2.53 (m, 2H), 2.51-2.40 (m, 4H), 2.25 (m, 5H), 2.10 (s, 3H), 1.81 (d, J=10.2 Hz, 2H), 1.55-1.42 (m, 2H). MS: ESI m/z 620.2 [M+H]+.

Experimental Example 1: Measurement of Kinase Inhibitory Activity

The inhibitory activity on a C797S-containing epidermal growth factor receptor (EGFR) kinase and an MET kinase was measured for compound 1 obtained in the above Example, and the results are shown in Table 1 below. The kinase inhibitory activity was measured by the following method:

1. Each kinase was incubated with 8 mM MOPS (pH 7.0), 0.2 mM EDTA, 250 μM KKKGQEEEYVFIE (SEQ ID NO: 1), 1 mM sodium orthovanadate, 5 mM sodium-6-glycerophosphate, 10 mM magnesium acetate, and [η-$^{33}$P]-ATP.
2. The compound to be evaluated (DMSO solution) and Mg/ATP were added to proceed the reaction.
3. After about 40 minutes at room temperature, the reaction was stopped by the addition of 10 μL of 0.5% phosphoric acid.
4. 10 μL of 0.5% reaction solution was spotted onto a P30 filtermat.
5. Washed 4 times for about 4 minutes in 0.425% phosphoric acid. Washed once in methanol, and then dried and analyzed by scintillation counting to measure IC$_{50}$ value.

TABLE 1

| Example | EGFR (del19/C797S) | EGFR (del19/T790M/C797S) | MET (IC$_{50}$) |
|---|---|---|---|
| 1 | 0.4 nM | 0.08 nM | 1 nM |
| Brigatinib | — | 2 nM | 70 nM |
| TRE-069 | — | 6 nM | 120 nM |

As shown in the experimental results of Table 1 above, it was confirmed that the compounds prepared according to the Examples of the present invention were very superior in inhibitory activity on a C797S-containing epidermal growth factor receptor (EGFR) kinase and an MET kinase compared to brigatinib and TRE-069.

Experimental Example 2: Measurement of Inhibitory Effect on Cancer Cell Growth The inhibitory effect on the growth of a C797S-expressed triple mutant Ba/F3 cancer cell line was measured for the compounds obtained in the examples above. The kinase assay and anticancer efficacy activity using a Ba/F3 stable cell line were measured by the following method:

1. Gene construction: Wild type and mutant EGFR were purchased from Addgene (wild type, #11011; L858R, #11012; L858R+T790M, #32073; del19, #32062; del19+T790M, #32072). All constructs were retroviral vectors and finally completed viral particles for infection.
2. Construction of Ba/F3 stable cell lines: Murine lymphoid cells undergo IL-3 dependent growth. Infection of each mutant EGFR construct into these cell lines results in oncogenic addiction due to the expression of mutant EGFR, thereby allowing cells to survive without IL-3. Using this principle, a stable cell line was constructed even without puromycin selection. Briefly, each construct was infected into Ba/F3 cell lines, and after 48 hours, IL-3 was removed with media exchange and cells were cultured. However, puromycin selection was performed for wild type EGFR.
3. Identification of Ba/F3 stable cell lines: All stable cell lines were subjected to western blotting to confirm the expression of each construct and EGFR activity (EGFR wild type and L858R were omitted).

4. Confirmation of changes in cellular kinase activity (Western blotting): Cells were obtained after 5 hours treatment of drugs in a concentration-dependent manner in each stable cell line. EBC lysis buffer (50 mM Tris-HCl (pH 8.0), 120 mM NaCl, 1% Triton X-100, 1 mM EDTA, 1 mM EGTA, 0.3 mM phenylmethylsulfonylfluoride, 0.2 mM sodium orthovanadate, 0.5% NP-40, and 5 U/mL aprotinin) was used to make cell lysates. Antibodies of EGFR-related signaling molecules [p-EGFR (Tyr1173), EGFR, Akt, p-Erk, Erk, actin, from SantaCruz; p-Akt, from Cell signaling] were used to measure activity.

5. Anticancer effect verification by MTT assay: $2 \times 10^3$ cells were seeded in a 96-well plate. After 24 hours, each of the drugs was treated in a dose-dependent manner, incubated for 72 hours, reacted with 15 μL of MTT reagent for 4 hours, and then 100 μL of 10% SDS was added thereto and incubated for 24 hours. Changes in final OD were read at 595 nm. MTT results were analyzed by measuring $IC_{50}$ values through prism software.

Each compound was calculated as a $GI_{50}$ value, which is the concentration for 50% of inhibition of cell growth, and the results are shown in Table 2 below. Brigatinib and TRE-069 were used as a control drug.

TABLE 2

| Example | DEL19/ T790M/C797S ($IC_{50}$) | L858R/ T790M/C797S ($IC_{50}$) |
|---|---|---|
| 1 | 210 nM | 160 nM |
| 2 | 222 nM | 533 nM |
| 3 | 323 nM | 531 nM |
| *Brigatinib | 560 nM | 860 nM |
| **TRE-069 | 5,005 nM | 3,995 nM |

*Brigatinib: Nat. Commun. 2017 Mar. 13, 8: 14768.
**TRE-069: Bull. Korean Chem. Soc. 2017, Vol. 38, 1353-1357.

As shown in the experimental results of Table 2 above, it was confirmed that the compound prepared according to the Example of the present invention were very remarkable in inhibitory activity on C797S mutant epidermal growth factor receptor-expressed cancer cell lines compared to brigatinib and TRE-069. On the other hand, brigatinib and TRE069 were confirmed to be very less active compared to the compounds according to the Examples of the present invention.

The invention claimed is:

1. A compound of following Chemical Formula 1 or a pharmaceutically acceptable salt thereof:

[Chemical Formula 1]

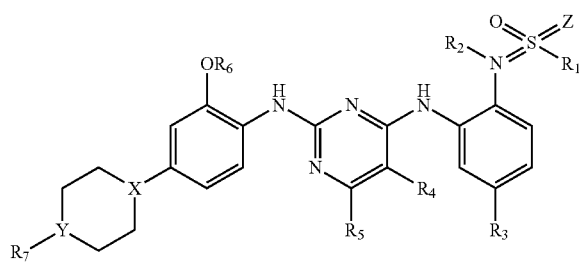

wherein,
X and Y are each independently carbon or nitrogen,
Z is oxygen or a C1 to C4 alkyl group,
$R_1$ is a C1 to C4 alkyl group, a C3 to C6 cycloalkyl group, $CF_3$, or a dimethylamine group,
$R_2$ is a C1 to C4 alkyl group,
$R_3$ is hydrogen or a halogen group,
$R_4$ is hydrogen, a halogen group, CN, $CF_3$, a C1 to C4 alkyl group, or an amino carbonyl group,
$R_5$ is hydrogen or a C1 to C4 alkyl group,
$R_6$ is a C1 to C4 alkyl group,
$R_7$ is hydrogen, an amine group substituted with one or more C1 to C4 alkyl groups, or a piperazinyl group unsubstituted or substituted with one or more C1 to C4 alkyl groups,
when Z is oxygen, Z forms a double bond with S, which forms a single bond with N, or when Z is a C1 to C4 alkyl group, Z forms a single bond with S, which forms a double bond with N, and
$R_4$ and $R_5$ may also be connected to form pyrrole, imidazole, or thiophene.

2. The compound or a pharmaceutically acceptable salt thereof according to claim 1, wherein the compound of Chemical Formula 1 is selected from the following compounds:
N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide;
N-(2-((5-chloro-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide;

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Lys Lys Lys Gly Gln Glu Glu Glu Tyr Val Phe Ile Glu
1               5                   10

N-(2-((5-chloro-2-((4-(4-(dimethylamino)piperidin-1-yl)-2-methoxyphenyl)amino)pyrimidin-4-yl)amino)phenyl)-N-methylmethanesulfonamide;

N-(2-((5-chloro-2-((2-methoxy-4-(4-(4-methylpiperazin-1-yl)piperidin-1-yl)phenyl)amino)pyrimidin-4-yl)amino)phenyl)-N,P,P-trimethylphosphonic amide;

N-(2-((2-((2-methoxy-4-(4-(4-methylpiperazin-1-yl)piperidin-1-yl)phenyl)amino)-7H-purin-6-yl)amino)phenyl)-N-methylmethanesulfonamide;

N-(2-((2-((2-methoxy-4-(4-(4-methylpiperazin-1-yl)piperidin-1-yl)phenyl)amino)-5-methylpyrimidin-4-yl)amino)phenyl)-N-methylmethanesulfonamide;

N-(2-((5-cyano-2-((2-methoxy-4-(4-(4-methylpiperazin-1-yl)piperidin-1-yl)phenyl)amino)pyrimidin-4-yl)amino)phenyl)-N-methylmethanesulfonamide;

N-(2-((2-((2-methoxy-4-(4-(4-methylpiperazin-1-yl)piperidin-1-yl)phenyl)amino)-5-(trifluoromethyl)pyrimidin-4-yl)amino)phenyl)-N-methylmethanesulfonamide;

2-((2-methoxy-4-(4-(4-methylpiperazin-1-yl)piperidin-1-yl)phenyl)amino)-4-((2-(N-methylmethylsulfonamido)phenyl)amino)pyrimidin-5-carboxylamide;

N-(2-((5-chloro-2-((2-methoxy-4-(4-(4-methylpiperazin-1-yl)piperidin-1-yl)phenyl)amino)pyrimidin-4-yl)amino)phenyl)-N-methylethanesulfonamide;

N-(2-((5-chloro-2-((2-methoxy-4-(4-(4-methylpiperazin-1-yl)piperidin-1-yl)phenyl)amino)pyrimidin-4-yl)amino)phenyl)-N-methylpropan-2-sulfonamide;

N-(2-((5-chloro-2-((2-methoxy-4-(4-(4-methylpiperazin-1-yl)piperidin-1-yl)phenyl)amino)pyrimidin-4-yl)amino)phenyl)-N-methylcyclopropansulfonamide;

N-(2-((5-chloro-2-((2-methoxy-4-(4-(4-methylpiperazin-1-yl)piperidin-1-yl)phenyl)amino)pyrimidin-4-yl)amino)phenyl)-1,1,1-trifluoro-N-methylmethanesulfonamide;

N-(2-((5-chloro-2-((2-methoxy-4-(4-(4-methylpiperazin-1-yl)piperidin-1-yl)phenyl)amino)pyrimidin-4-yl)amino)phenyl)-N-methyl(-N',N'-dimethyl)sulfonamide;

((2-((5-chloro-2-((2-methoxy-4-(4-(4-methylpiperazin-1-yl)piperidin-1-yl)phenyl)amino)pyrimidin-4-yl)amino)phenyl)imino)dimethyl-$\lambda^6$-sulfanone;

N-(2-((5-cyano-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide;

N-(2-((5-chloro-2-((2-methoxy-4-(piperidin-4-yl)phenyl)amino)pyrimidin-4-yl)amino)phenyl)-N-methylmethanesulfonamide; and N-(2-((2-((2-methoxy-4-(4-(4-methylpiperazin-1-yl)piperidin-1-yl)phenyl)amino)-7H-pyrrolo[2,3-d]pyrimidin-4-yl)amino)phenyl)-N-methylmethanesulfonamide.

3. The compound or a pharmaceutically acceptable salt thereof according to claim 1, wherein X is nitrogen,
Y is carbon,
Z is oxygen,
$R_1$ is a C1 to C4 alkyl group,
$R_2$ is a C1 to C4 alkyl group,
$R_3$ is hydrogen or a halogen group,
$R_4$ is a halogen group,
$R_5$ is hydrogen,
$R_6$ is a C1 to C4 alkyl group, $R_7$ is an amine group substituted with one or more C1 to C4 alkyl groups, or a piperazinyl group unsubstituted or substituted with one or more C1 to C4 alkyl groups.

4. The compound or a pharmaceutically acceptable salt thereof according to claim 3, wherein the compound of Chemical Formula 1 is selected from the following compounds:

N-(2-((5-chloro-2-((2-methoxy-4-(4-(4-methylpiperazin-1-yl)piperidin-1-yl)phenyl)amino)pyrimidin-4-yl)amino)phenyl)-N-methylmethanesulfonamide;

N-(2-((5-chloro-2-((2-methoxy-4-(4-(4-methylpiperazin-1-yl)piperidin-1-yl)phenyl)amino)pyrimidin-4-yl)amino)-4-fluorophenyl)-N-methylmethanesulfonamide; and N-(2-((5-chloro-2-((4-(4-(dimethylamino)piperidin-1-yl)-2-methoxyphenyl)amino)pyrimidin-4-yl)amino)phenyl)-N-methylmethanesulfonamide.

5. The compound or a pharmaceutically acceptable salt thereof according to claim 1, wherein the pharmaceutically acceptable salt is a salt of an acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, benzoic acid, hydroxybenzoic acid, phenylacetic acid, cinnamic acid, salicylic acid, methanesulfonic acid, ethanesulfonic acid, benzenesulfonic acid, and toluenesulfonic acid.

6. A pharmaceutical composition comprising the compound or the pharmaceutically acceptable salt thereof according to claim 1 as an active ingredient, and a pharmaceutically acceptable carrier.

7. A pharmaceutical composition comprising the compound or the pharmaceutically acceptable salt thereof according to claim 2 as an active ingredient, and a pharmaceutically acceptable carrier.

8. A pharmaceutical composition comprising the compound or the pharmaceutically acceptable salt thereof according to claim 3 as an active ingredient, and a pharmaceutically acceptable carrier.

9. A pharmaceutical composition comprising the compound or the pharmaceutically acceptable salt thereof according to claim 4 as an active ingredient, and a pharmaceutically acceptable carrier.

10. A pharmaceutical composition comprising the compound or the pharmaceutically acceptable salt thereof according to claim 5 as an active ingredient, and a pharmaceutically acceptable carrier.

11. A method for treating lung cancer in a subject in need thereof comprising administering the composition of claim 6 to the subject.

12. A method for treating lung cancer in a subject in need thereof comprising administering the composition of claim 7 to the subject.

13. A method for treating lung cancer in a subject in need thereof comprising administering the composition of claim 8 to the subject.

14. A method for treating lung cancer in a subject in need thereof comprising administering the composition of claim 9 to the subject.

15. A method for treating lung cancer in a subject in need thereof comprising administering the composition of claim 10 to the subject.

\* \* \* \* \*